United States Patent [19]
Arcamone et al.

[11] Patent Number: 5,641,802
[45] Date of Patent: Jun. 24, 1997

[54] TACHYQUININE ANTAGONISTS, THEIR PREPARATION AND USE IN PHARMACEUTICAL FORMULATIONS

[75] Inventors: Federico Arcamone, Nerviano; Paolo Lombardi, Cesate; Stefano Manzini, Florence; Edoardo Potier; Alessandro Sisto, both of Rome, all of Italy

[73] Assignees: A. Menarini Industrie Farmaceutiche Reiunite S.r.l.; Malesci Istituto Farmacobiologico S.p.A., Florence, Italy

[21] Appl. No.: 448,460

[22] PCT Filed: Dec. 2, 1993

[86] PCT No.: PCT/EP93/03387

§ 371 Date: Jun. 2, 1995

§ 102(e) Date: Jun. 2, 1995

[87] PCT Pub. No.: WO94/13694

PCT Pub. Date: Jun. 23, 1994

[30] Foreign Application Priority Data

Dec. 4, 1992 [IT] Italy .................. MI92A2779

[51] Int. Cl.$^6$ .................. A61K 31/40; C07D 209/12
[52] U.S. Cl. .................. 514/419; 514/255; 514/323; 514/339; 544/373; 544/405; 546/201; 546/278.1; 548/492
[58] Field of Search .................. 514/255, 323, 514/339, 419; 544/373, 405; 546/201, 273; 548/492

[56] References Cited

U.S. PATENT DOCUMENTS 5,164,372 11/1992 Matsuo et al. .

FOREIGN PATENT DOCUMENTS

| 0333174 | 9/1989 | European Pat. Off. . |
| 0394989 | 10/1990 | European Pat. Off. . |
| 0482539 | 4/1992 | European Pat. Off. . |
| 9314113 | 7/1993 | WIPO . |

OTHER PUBLICATIONS

R.M. Snider et al., *A Potent Nonpeptide Antagonist of the Substance P ($NK_1$) Receptor*, Science, vol. 25, 25 Jan. 1991, pp. 435–447.

T. Fujii et al., *Pharmacological Profile of a High Affinity Dipeptide $NK_1$ Receptor Antagonist, FK888* Br. J. Pharmacol. (1992) 107, pp. 785–789.

D.G. Payan, et al., *Stereospecific Receptors For Substance P On Cultured Human IM–9 Lymphoblasts*. The Journal of Immunology, vol. 133, Dec. 6, 1984, pp. 3260–3265.

D. Regoli et al, *Substance P — Structure–Activity Studies and the Development of Antagonists*, Pharmacology 28:301–320 (1984).

Primary Examiner—Jacqueline Haley
Attorney, Agent, or Firm—Kenyon & Kenyon

[57] ABSTRACT

A description is given of tachyquinine antagonists having general formula (I)

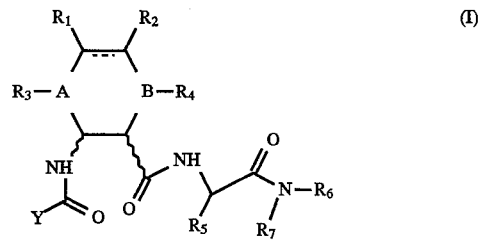

their preparation and use in pharmaceutical formulations.

8 Claims, No Drawings

TACHYQUININE ANTAGONISTS, THEIR PREPARATION AND USE IN PHARMACEUTICAL FORMULATIONS

This application is a National Stage application of PCT/EP93/03387, filed Dec. 2, 1993 and published on Jun. 23, 1994 as WO 94/13694.

FIELD OF THE INVENTION

The present invention refers to tachyquinine antagonists, their preparation and use in pharmaceutical formulations.

In particular, the present invention refers to compounds having general formula (I)

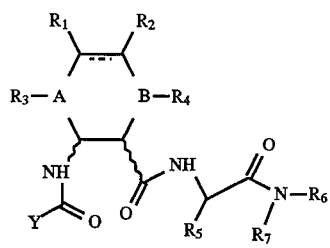

wherein:

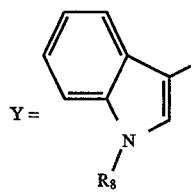

where $R_8$ is selected out of a group consisting of H, a linear or branched alkyl radical containing 1 to 6 carbon atoms, a linear or branched alkenyl radical containing 2 to 7 carbon atoms, a linear or branched alkynyl radical containing 3 to 7 carbon atoms, a cycloalkyl radical containing 3 to 6 carbon atoms, possibly substituted with at least one atom selected out of a group consisting of N, S, and O, an aryl-, aryl-alkyl-, alkyl-aryl-radical containing 7 to 12 carbon atoms;

symbol ≡ represents a single or a double bond: if the bond is single, $R_1$ and $R_2$ are selected out of a group consisting of hydrogen, hydroxyl and halogen or are joined to form an epoxide; if the bond is double, they are hydrogen or halogen; A and B stand for N or CH; $R_3$ and $R_4$ are selected out of the group consisting of hydrogen, a linear or branched alkyl radical containing 1 to 6 carbon atoms, a linear or branched alkenyl radical containing 2 to 7 carbon atoms, a linear or branched alkynyl radical containing 3 to 7 carbon atoms, or are joined together to form a —$(CH_2)_n$— bridge, where n stands for a whole number from 1 to 3;

$R_5$ stands for an alkyl-, aryl-, aryl-alkyl- or alkyl-aryl-radical with 15 carbon atoms max.;

$R_6$ and $R_7$ are selected out of a group consisting of hydrogen, an alkyl -, aryl-, aryl-alkyl- or alkyl-aryl-radical as defined above.

Symbol ∩∩∩ means that the configuration of the asymmetric carbon atoms of 2-amino-cyclohexanecarboxylic acid is S or R, with the proviso that such configuration can not be S or R for both the asymmetric carbon atoms.

Tachyquinine antagonist compounds as per formula (I) prove to be effective in the treatment of diseases where tachyquinines play a pathogenic role, in particular in the treatment of arthritis, asthma, inflammations, tumoral growth, gastrointestinal hypermotility, Huntington's disease, neuritis, neuralgia, migraine, hypertension, incontinence of urine, urticaria, carcinoid syndrome symptoms, influenza, and cold.

State of the art

Tachyquinines are a family of three peptides at least, known as substance P (SP), neuroquinine A (NKA) and neuroquinine B (NKB).

Research in the field of tachyquinine antagonists, initially directed toward single or multiple replacement of amino acids of the peptide agonists sequence of Substance P and of the other tachyquinines, brought to the discovery of non-apeptides containing one or more D-tryptophan units [Regoli et al., Pharmacol., 28, 301 (1984)].

On the other hand, the problems related to the use of high-molecular-weight peptides as drugs (multiplicity of enzymatic hydrolytic attack sites, poor bioavailability, rapid excretion from the liver and kidneys) spurred to search for the minimum peptide fragment still capable of exerting an antagonist action. These studies brought to the singling out of suitably derivatized SP antagonists tripeptides and dipeptides (European patents Nos. 333174 and 394989, in the latter α-amino-acids wherein the N-atom is s member of a ring-structure are described).

In Br J Pharmacol 107 (1992) 785–9, an high affinity dipeptide $NK_1$ receptor antagonist, i.e.: $N^2$-[(4R)-4-hydroxy-1-(1-methyl-1H-indol-3-yl)carbonyl-L-propyl]-N-methyl-N-phenylmethyl-3-(2-naphthyl)-L-alaninamide, is described.

In Science 251 (1991) 435, (2S,3C)-cis-2-(diphenylmethyl)-N-[(2-methoxyphenyl)-methyl]-1-azabicyclo[2.2.2.]octan-3-amine is described as potent non-peptide antagonist of the Substance P ($NK_1$) receptor.

DETAILED DESCRIPTION OF THE INVENTION

It has surprisingly been found—and this finding constitutes a fundamental feature of the present invention—that non-peptidic compounds of general formula (I) as defined above are good inhibitors of the tachyquinines bond to $NK_1$ receptor and have a sufficient metabolic stability.

Particularly preferred products are compounds of general formula (I) wherein:

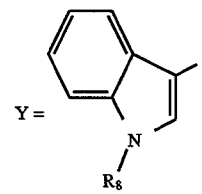

and $R_8$=H, $R_5$ and $R_6$=

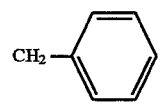

and $R_1$, $R_2$, $R_3$, $R_4$, $R_7$, A, and B are as defined above.

The present description sets forth the following substituent groups as particularly preferred: the alkyl radical is selected out of a group consisting of methyl, ethyl, propyl, butyl, and pentyl; the alkenyl radical is selected out of the group consisting of propenyl and butenyl; the alkynyl radical is propynyl; possibly substituted aryl-, alkyl-aryl- and aryl-alkyl-radicals present preferably an alkyl radical as defined above, while the aryl moiety is preferably possibly substituted pyridine, benzofuran, benzene, indole, naphthyl, tetrahydroquinoline, imidazole, tetrahydroindoline; a cycloalkyl radical, possibly substituted at least with an atom selected out of a group consisting of N, S and O, is preferably selected out of a group consisting of cyclohexane, cyclopentane, cycloheptane, cyclooctane, piperidine, morpholine, piperazine, and pyrazine.

In view of the asymmetry centres of formula (I), this invention refers to the various diastereoisomers of said formula; in particular, substituent $R_5$ is preferably in S-position.

The compounds under the present invention proved to be SP, Neuroquinine A, and Neuroquinine B antagonists. Therefore, they can be utilized for the prevention and treatment of diseases where tachyquinines (SP, NKA, NKB) play a neuromodulating role, such as respiratory conditions (e.g. asthma, allergic rhinitis), ophthalmic conditions (e.g. conjunctivitis), cutaneous conditions (e.g. allergic dermatitis, dermatitis by contact, psoriasis), intestinal conditions (e.g. ulcerative colitis, Crohn's disease).

Another fundamental object of the invention is the preparation of compounds of formula (I) by condensation.

Compounds of general formula (I) as defined above are prepared via the steps of:

a) condensing, in the presence of a suitable condensing agent, intermediate of formula (II)

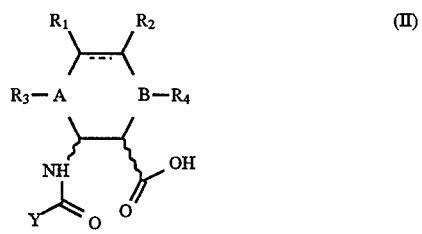

with intermediate of formula (III)

where $R_1$, $R_2$, $R_3$, $R_4$, $R_5$, $R_6$, $R_7$, Y, A, and B are as defined above, said compound of formula (II) being prepared by condensation, in the presence of a suitable condensing agent, of a compound of general formula (IV) with a derivative of the acid of general formula (V), suitably substituted on the ring and possibly protected on the hydroxyl group of the ring by a group of the tert-butyl type, followed by elimination of the carboxylic end group

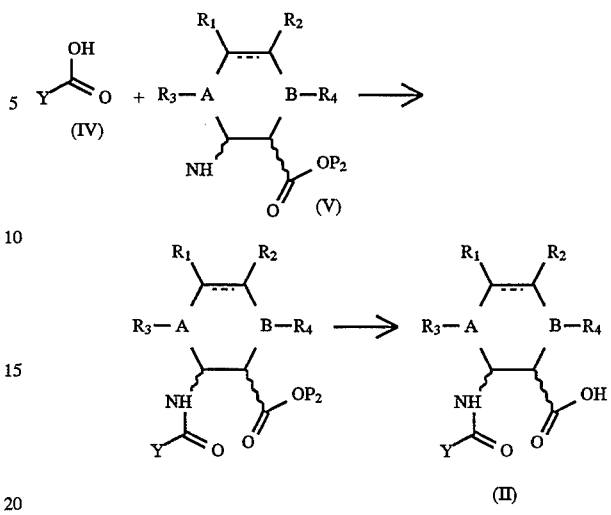

where $R_1$, $R_2$, $R_3$, $R_4$, Y, A, and B are as defined above and $P_2$ is a group that temporarily protects the carboxylic group, in particular the ester used is a methyl ester and the successive carboxyl elimination is carried out by basic hydrolysis, and intermediates of general formula (III) being prepared by condensation of amino acid derivative of general formula (VI) and amine of general formula (VII)

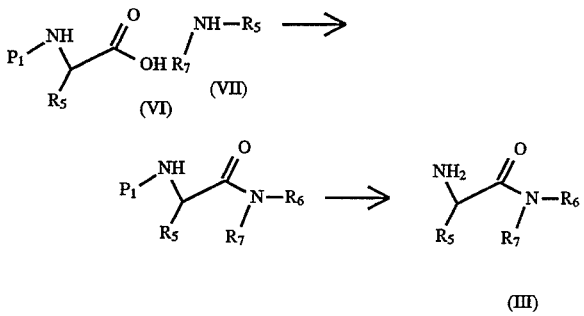

where $R_5$, $R_6$, $R_7$ are as defined above and $P_1$ is a group protecting the α-amino group, selected out of the groups commonly used in classical peptide syntheses, which can be easily removed under conditions not causing the partial of total opening of the bond between $R_6$, $R_7$ and nitrogen. In particular, $P_1$ is preferably a tert-butyloxycarbonyl of fluorenylmethyloxycarbonyl group and can be removed by acidolysis of basic treatment, respectively, wherein the benzyl groups, if any, bound to the substituted amide are stable, said condensation being carried out at room temperature in the presence of aprotic polar organic solvents capable of solubilizing the reagents and not negatively interfering with the reaction progress;

b) eliminating the reaction by-products by evaporation of the reaction solvent and treatment of the residue, or a solution of same in a suitable organic solvent, with slightly acid or slightly basic aqueous solutions;

c) separating the residue obtained under b) by chromatography or crystallization.

The reaction solvents mentioned under a) and b) are selected out of the group consisting of dimethylformamide, dioxane, tetrahydrofuran, halogenated aliphatic hydrocarbons, methylene chloride, dichloroethane.

Excellent product yield and purity were obtained using benzotriazolyloxy tripyrrolidine phosphonium hexafluorophosphate (PyBop) as a condensing agent. In particular, the reaction was carried out by addition of slight excess of PyBop to a carboxylic component (formula II) solution, maintained at low temperature, followed by addition of the aminic component hydrochloride (formula VI) and a quantity of tertiary amine of three equivalents in respect of the condensing agent.

An alternative procedure envisages the use, as a condensing agent, of 1-ethyl-3-(3'-dimethylaminopropyl)-carbodiimide.

A further object of the present invention is the synthesis procedure of intermediate of general formula (II) and the product obtained therefrom (intermediate II).

The compounds of this invention can exist in different isomeric configurations. In fact, the configuration of the carbon atom bound to substituent $R_5$ is univocally determined by the synthesis starting compound being of formula VI. However, the other starting compound (i.e. 2-aminocyclohexanecarboxylic acid as per formula II) has 2 asymmetric carbon atoms and usually consists of an inseparable mixture of two enantiomers, whose ring substituents are either cis or trans. It follows that the compounds of this invention are mixtures of diastereoisomers (two having trans ring substituents and two having cis substituents). Said mixtures can be easily resolved by chromatography. In any case, compounds of formula (I) can be used both in optically active form and in the form of isomeric mixtures.

The following examples illustrate some embodiments of the claimed invention and the synthesis procedure thereof.

EXAMPLE 1 (FOR REFERENCE)

N-methyl-N-benzylamide of $N^\alpha$-{[N(indol-3-yl-carbonyl)(R,R)-trans-2-amino]cyclohexanoyl}-L-phenylalanine and N-methyl-N-benzylamide of $N^\alpha$-{[N(indol-3-yl-carbonyl)(S,S)-trans-2-amino]cyclohexanoyl}-L-phenylalanine 1) Methyl ester hydrochloride of trans-2-amino-cyclohexanecarboxylic acid (HCl,H-trans-2-$Ac^6c$-OMe)

(Abbreviations 2-$Ac^6c$ stands for 2-amino cyclohexanecarboxylic acid and I3c means the indolin-3-yl-carbonyl residue).

Trans H-2-$Ac^6c$-OH (500 mg) was suspended, at room temperature, in a saturated solution of hydrochloric acid in methyl alcohol (7.5 ml). After 24-hr stirring at room temperature the solution was limpid.

The resulting solution was evaporated to dryness by nitrogen blowing; the residue was repeatedly taken up with methyl alcohol (4×15 ml) and evaporated to dryness for excess hydrochloric acid elimination.

The product was isolated by grounding with diethyl ether 3×10 ml). Obtained 648 mg.

The $R_f$ value obtained by thin layer chromatography (TLC) (eluent: chloroform/methanol/acetic acid (CMA), 85/10/5) was 0.25.

2) Methyl ester of N-(indol-3-yl-carbonyl)-trans-2-aminocyclohexanecarboxylic acid (I3c-trans-2-$Ac^6c$-OMe)

A suspension of the product obtained under 1) (500 mg) in dichloromethane (DCM) (5 ml) was cooled to 0° C., stirred under nitrogen atmosphere, and added with 402 mg indolyl-3-carboxylic acid (I3c-OH), 337 mg 1-hydroxybenzotriazole (HOBt), 488 mg 1-ethyl-3-(3'-dimethylamino propyl)carbodiimide (WSC), and 0.52 ml diisopropylethylamine (DiPEA). The limpid solution was allowed to stir for 45 min at 0° C. and for additional 16 hrs at room temperature. The solvent was eliminated by evaporation under reduced pressure and the residue was taken up with ethyl acetate (EtOAc) (50 ml). The organic solution was extracted with a 5% $NaHCO_3$ aqueous solution (3×50 ml), with an NaCl saturated aqueous solution (3×50 ml), with a 0.1N HCl aqueous solution (3×50 ml), and again with an NaCl saturated aqueous solution (3×50 ml). The organic phase, after water elimination on $Na_2SO_4$, was evaporated to dryness to give a white powder (583 mg, yield 78%).

HPCL was carried out with 5 mm Spherisorb® ODS-2 (150×4.6 mm) column eluting with:

A=0.1% trifluoroacetic acid in acetonitrile;
B=0.1% trifluoroacetic acid in water;
gradient outline 20% to 80% of A at 25 min;
flow rate 1 ml/min; effluent monitored at 230 nm (UV detector).

HPLC analysis showed a single peak at retention time $(R_t)$=15.83 min.

The $R_f$ value obtained by thin layer chromatography (TLC) (eluent: ethyl acetate/hexane, 80/20 v/v) was 0.31.

3) N-(indol-3-yl-carbonyl)-trans-2-aminocyclohexanecarboxylic acid (I3c-trans-2-$Ac^6c$-OH)

A suspension of the product obtained under 2) above (500 mg) in 5% NaOH (9 ml) was allowed to stir for 36 hrs at room temperature. The limpid solution was maintained at 0° C. and under vigorous stirring, extracted with EtOAc (15 ml×3) and acidified with 0.1N HCl to pH 3.

The product was isolated by filtering the precipitate that forms and drying under reduced pressure (402 mg, yield 84%).

The $R_f$ value obtained by thin layer chromatography (TLC) (eluent: chloroform/methyl alcohol (CM), 80/20 v/v) was 0.29.

HPLC analysis as per step 2 showed a single peak at $R_t$=12.96 min.

4) N-methyl-N-benzyl amide of N(tert-butyloxycarbonyl)-L-phenylalanine (Boc-Phe-NMeBz)

A solution of N-(tert-butyloxycarbonyl)-L-phenylalanine (5 g) in anhydrous dichloromethane (10 ml) was vigorously stirred at 0° C. under nitrogen atmosphere, added with N-methyl-N-benzylamine (2.66 ml), bromotripyrrolidinephosphonium hexafluorophosphate (PyBroP), and slowly with DiPEA (6.55 ml). The solution was allowed to stir for 30 min at 0° C. and for additional 4 hrs at room temperature. The solvent was eliminated by evaporation under reduced pressure and the residue was taken up with EtOAc (50 ml).

The organic solution was extracted with a 5% $NaHCO_3$ aqueous solution (3×50 ml), with an NaCl saturated aqueous solution (3×50 ml), with a 0.1N HCl aqueous solution (3×50 ml), and again with an NaCl saturated aqueous solution (3×50 ml). The organic phase, after water elimination on $Na_2SO_4$, was evaporated to dryness to give a pale yellow oil, which was crystallized from 20 ml ethanol/water mixture (50/50 v/v). The product was isolated by filtering the precipitate and drying under reduced pressure (4.86 g, yield 70%).

HPLC analysis as per step 2, showed a single peak at $R_t$=24.11 min.

The $R_f$ value obtained by thin layer chromatography (TLC) (eluent: CM, 90/10 v/v) was 0.80.

5) N-methyl-N-benzyl amide hydrochloride of L-phenylalanine (HCl H-Phe-NMeBz)

A suspension of the product obtained under 4) above (1.0 g) in ca. 2N HCl saturated EtOAc solution was allowed to stir for 2 hrs at room temperature. The solvent was eliminated by slight nitrogen blowing and the residue was repeatedly suspended with ethyl ether (4× 30 ml) and evaporated to dryness. The product obtained was a white powder (0.669 g, yield 80%).

The $R_f$ value obtained by thin layer chromatography (TLC) (eluent: CM) was 0.68.

HPLC analysis as per step 2 showed a single broad peak at $R_t$=16.03 min.

6) N-methyl-N-benzylamide of $N^\alpha$-{[N(indol-3-yl-carbonyl)(R,R)-trans-2-amino]cyclohexanoyl}-L-phenylalanine
and N-methyl-N-benzylamide of $N^\alpha$-{[N(indol-3-yl-carbonyl)(S,S)-trans-2-amino]cyclohexanoyl}-L-phenylalanine A suspension of the product obtained under 3) above (50 mg) in DCM (5 ml) was cooled to 0° C., allowed to stir under nitrogen atmosphere and added with the product obtained under 5) above (52 mg), benzotriazolyloxy tripyrrolidine phosphonium hexafluorophosphate (PyBop) (106 mg) and DiPEA (0.080 ml). After clarification, the solution was allowed to stir for 45 min at 0° C. and for additional 16 hrs at room temperature. The solvent was eliminated by evaporation under reduced pressure and the residue was taken up with EtOAc (50 ml).

The organic solution was added with 5% NaHCO$_3$ aqueous solution (50 ml), and the resulting solution was allowed to stir for 20 min at room temperature. The organic phase was separated and extracted with a 5% NaHCO$_3$ aqueous solution (3×50 ml), with an NaCl saturated aqueous solution (3×50 ml), with a 0.1N HCl aqueous solution (3× 50 ml), and again with an NaCl saturated aqueous solution (3×50 ml). The organic phase, after water elimination on Na$_2$SO$_4$, was evaporated to dryness yielding a pale yellow residue (85 mg, yield 93%).

The two diastereoisomers were separated by reversed-phase 7μ Lichrosorb® RP-18 column (Hibar Merck®) eluting with 48% acetonitrile aqueous mixture containing 0.1% trifluoroacetic acid.

The fractions corresponding to the two peaks of the two isolated diastereoisomers were joined, concentrated to small volume at a reduced pressure and repeatedly freeze-dried.

HPLC analysis under isocratic conditions at 52% of A showed a single peak for each of the two products (denominated "fast" and "slow" depending on their being eluted at an earlier or, respectively, at a later time):

HPLC (fast)=10.50 min HPLC (slow)=11.03 min.

EXAMPLE 2

N-methyl-N-benzylamide of $N^\alpha$-{[N(indol-3-yl-carbonyl)(R,S)-cis-2-amino]cyclohexanoyl}-L-phenylalanine and N-methyl-N-benzylamide of $N^\alpha$-{[N(indol-3-yl-carbonyl)(S,R)-cis-2-amino]cyclohexanoyl}-L-phenylalanine 1b) Methyl ester hydrochloride of cis-2-amino-cyclohexanecarboxylic acid (HCl,H-cis-2-Ac$^6$c-OMe)

Cis H-2-Ac$^6$c-OH (500 mg) was suspended, at room temperature, in a saturated solution of hydrochloric acid in methyl alcohol (7.5 ml). After 24-hr stirring at room temperature the solution was limpid.

The resulting solution was evaporated to dryness by nitrogen blowing; the residue was repeatedly taken up with methyl alcohol (4×15 ml) and evaporated to dryness for excess hydrochloric acid elimination.

The product was isolated by grounding with diethyl ether (3×10 ml). Yield 618 mg.

The $R_f$ value obtained by thin layer chromatography (TLC) (eluent: CMA) was 0.25.

2b) Methyl ester of N-(indol-5-yl-carbonyl)-cis-2-amino-cyclohexanecarboxylic acid (I3c-cis-2-Ac$^6$c-OMe)

A suspension of the product obtained under 1b) (500 mg) in DCM (5 ml) was cooled to 0° C., allowed to stir under nitrogen atmosphere, and added with 402 mg I3c-OH, 337 mg HOBt, 488 mg WSC, and 0.52 ml DiPEA. The limpid solution was allowed to stir for 45 min at 0° C. and for additional 16 hrs at room temperature. The solvent was eliminated by evaporation under reduced pressure and the residue was taken up with EtOAc (50 ml). The organic solution was extracted with a 5% NaHCO$_3$ aqueous solution (3×50 ml), with an NaCl saturated aqueous solution (3×50 ml), with a 0.1N HCl aqueous solution (3×50 ml), and again with an NaCl saturated aqueous solution (3×50 ml). The organic phase, after water elimination on Na$_2$SO$_4$, was evaporated to dryness. The residue was crystallized from ethyl alcohol/water to give a colourless microcrystalline product (610 mg, yield 85%).

HPCL was carried out as per 2) using 5μ Lichrosphe® 100 RP-18 column (250×4.6 mm) and showed a single peak at $R_t$=18.84 min.

The $R_f$ value obtained by thin layer chromatography (TLC) (eluent: CM) was 0.23.

3b) N-(indol-3-yl-carbonyl)-cis-2-amino-cyclohexanecarboxylic acid (I3c-cis-2-Ac$^6$c-OH)

A suspension of the product obtained under 2b) above (220 mg) in 5% NaOH (6.5 ml) was allowed to stir for 36 hrs at room temperature. The limpid solution was maintained at 0° C. and under vigorous stirring, extracted with EtOAc (15 ml×3) and acidified with 0.1N HCl to pH 3.

The product was isolated by filtering the precipitate that forms and drying under reduced pressure (146 mg, yield 70%).

The $R_f$ value obtained by thin layer chromatography (TLC) (eluent: chloroform/methyl alcohol, 80/20 v/v) was 0.50.

HPLC analysis as per step 2b showed a single peak at $R_t$=14.83 min.

4b) N-methyl-N-benzylamide of $N^\alpha$-{[N(indol-3-yl-carbonyl)(S,R)-trans-2-amino]cyclohexanoyl}-L-phenylalanine
and N-methyl-N-benzylamide of $N^\alpha$-{[N(indol-3-yl-carbonyl)(R,S)-trans-2-amino]cyclohexanoyl}-L-phenylalanine A suspension of the product obtained under 3b) above (70 mg) in DCM (7 ml) was cooled to 0° C., allowed to stir under nitrogen atmosphere, and added with HCl H-Phe-NMeBz (52 mg), PyBop (156 mg) and DiPEA (0.140 ml). The limpid solution was allowed to stir for 45 min at 0° C. and for additional 16 hrs at room temperature. The solvent was eliminated by evaporation under reduced pressure and the residue was taken up with EtOAc (50 ml).

The organic solution was added with 5% NaHCO$_3$ aqueous solution (50 ml), and the resulting solution was allowed to stir for 20 min at room temperature. The organic phase was separated and extracted with a 5% NaHCO$_3$ aqueous solution (2×50 ml), with an NaCl saturated aqueous solution (3×50 ml), with a 0.1N HCl aqueous solution (3×50 ml), and again with an NaCl saturated aqueous solution (3×50 ml). The organic phase, after water elimination on $Na_2SO_4$, was evaporated to dryness yielding a pale yellow residue (111 mg, yield 85%).

The two diastereoisomers were separated by reversed-phase 7μ Lichrosorb® RP-18 column (Hibar Merck®) eluting with 44% acetonitrile aqueous mixture containing 0.1% trifluoroacetic acid.

The fractions corresponding to the two peaks of pure diastereoisomers were joined, concentrated to small volume at a reduced pressure and repeatedly freeze-dried.

HPLC analysis under isocratic conditions at 56% of A showed a single peak for each of the two products (denominated "fast" and "slow" depending on their being eluted at an earlier or, respectively, at a later time):

HPLC (fast)=8.76 min HPLC (slow)=10.96 min

The following compounds were also obtained.

EXAMPLE 3

$N^\alpha$[N-(1H-indol-3-yl-carbonyl)-(R,S)cis-2-aminocyclohexyl-carbonyl]-L-3(2-naphthyl)alanyl-N-methyl-N-benzylamide and $N^\alpha$[N-(1H-indol-3-yl-carbonyl)-(S,R)cis-2-aminocyclohexyl-carbonyl]-L-3(2-naphthyl)alanyl-N-methyl-N-benzylamide HPLC: column Phase Sep. Spherisorb ODS-2 5 mm (250×4.6 mm) fitted with a Phase Sep. Spherisorb S5 ODS-2 (50×4.6 mm) precolumn; eluent A: $H_2O$, 0.1% trifluoroacetic acid; eluent B: Acetonitrile, 0.1% trifluoroacetic acid; UV Detection 215 nm; flow 1 ml/min; linear gradient from 20% to 80% B in 20 min, then isocratic 80% B for 10 min (HPLC System 1): fast: $T_R$=7.66 min slo $T_R$=8.69 min; TLC($SiO_2$) $CHCl_3/CH_3OH$ (9:1 v/v) $R_f$=0.4 and 0.4.

EXAMPLE 4

$N^{6\mathrm{o}}$[N-(1H-indol-3-yl-carbonyl)-(R,S)cis-2-aminocyclohexyl-carbonyl]-L-2-phenylalanyl-N-benzylamide and $N^\alpha$[N-(1H-indol-3-yl-carbonyl-(S,R)cis-2-aminocyclohexyl-carbonyl]-L-2-phenylalanyl-N-benzylamide HPLC: column Phase Sep. Spherisorb ODS-2 5 mm (250×4.6 mm) fitted with a Phase Sep. Spherisorb S5 ODS-2 (50×4.6 mm) precolumn; eluent A: $H_2O$, 0.1% trifluoroacetic acid; eluent B: Acetonitrile, 0.1% trifluoroacetic acid; UV Detection 215 nm; flow 1 ml/min; (HPLC system 2) isocratic 59% B; fast: $T_R$=7.66 min slow $T_R$=8.69 min. TLC ($SiO_2$)$CH_2Cl_2/CH_3OH$ (95:5 v/v) $R_f$=0.17 and 0.17.

EXAMPLE 5

$N^\alpha$[N-(1H-indol-3-yl-carbonyl)-(R,S)cis-2-aminocyclohexyl-carbonyl]-L-phenylalanyl-N,N dibenzylamide and $N^\alpha$[N-(1H-indol-3-yl-carbonyl)-(S,R)cis-2-aminocyclohexan-carboxyl]-L-phenylalanyl-N,N dibenzylamide HPLC: (System 2) isocratic 66% B; fast: $T_R$=13.94 min slow $T_R$=15.16 min; TLC($SiO_2$)$CH_2Cl_2/CH_3OH$ (95:5 v/v) $R_f$=0.23 and 0.31.

EXAMPLE 6

$N^\alpha$[N-(1-(methyl)indol-3-yl-carbonyl)-(R,S)cis-2-aminocyclohexylcarbonyl]-L-3(2-naphthyl)alanyl-N-methyl-N-benzylamide and $N^\alpha$[N-(1-(methyl)indol-3-yl-carbonyl)-(S,R)cis-2-aminocyclohexylcarbonyl]-L-3(2-naphthyl)alanyl-N-methyl-N-benzylamide HPLC:(System 1) fast: $T_R$=13.94 min slow $T_R$=15.16 min; TLC($SiO_2$) $CH_2Cl_2/CH_3OH$ (95:5 v/v) $R_f$=0.23 and 0.31.

EXAMPLE 7

$N^\alpha$[N-(1-(methyl)indol-3-yl-carbonyl)-(R,S)cis-2-aminocyclohexylcarbonyl]-L-phenylalanyl-N-methyl-N-benzylamide HPLC: (System 2) isocratic 70% B; $T_R$=9.94 min TLC ($SiO_2$) $CHCl_3/CH_3OH$ (90:10 v/v) $R_f$=0.65.

EXAMPLE 8

$N^\alpha$[N-(1H-indol-3-yl-carbonyl)-(R,S)cis-2-aminocyclohexyl-carbonyl]-L-phenylalanyl-N,N dimethylamide and $N^\alpha$[N-(1H-indol-3-yl-carbonyl)-(S,R)cis-2-aminocyclohexan-carbonyl]-L-phenylalanyl-N,N dimethylamide HPLC: (System 2) isocratic 52% B; fast: $T_R$=7.36 min slow $T_R$=9.70 min.

EXAMPLE 9

$N^\alpha$[N-(1H-indol-3-yl-carbonyl)-(R,S)cis-2-aminocyclohexyl-carbonyl]-L-phenylalanyl-tetrahydroisoquinolide and $N^\alpha$[N-(1H-indol-3-yl-carbonyl)-(S,R)cis-2-aminocyclohexan-carboxyl]-L-phenylalanyltetrahydroisoquinolide HPLC: (System 2) isocratic 65% B; fast: $T_R$=8.71 min slow $T_R$=10.74 min.

EXAMPLE 10

$N^\alpha$[N-(1H-indol-3-yl-carbonyl)-3S-endo aminobicyclo(2,2,1)heptyl-2R endo carbonyl]-L-3-(2-naphthyl)alanyl-N-methyl-N-benzylamide and $N^\alpha$[N-(1H-indol-3-yl-carbonyl)-3R-endo aminobicyclo(2,2,1)heptyl-2S-endo carbonyl]-L-3-(2-naphthyl)alanyl-N-methyl-N-benzylamide HPLC: (System 2) isocratic 60% B; fast: $T_R$=14.39 min slow $T_R$=15.54 min.

EXAMPLE 11

$N^\alpha$[N-(1H-indol-3-yl-carbonyl)-3S-exo-aminobicyclo(2,2,1)heptyl-2R-exo carbonyl]-L-3-(2-naphthyl)alanyl-N-methyl-N-benzylamide and $N^\alpha$[N-(1H-indol-3-yl-carbonyl)-3R-endo aminobicyclo(2,2,1)heptyl-2S-exo carbonyl]-L-3-(2-naphthyl)alanyl-N-methyl-N-benzylamide HPLC: (System 2) isocratic 70% B; fast: $T_R$=9.20 min slow $T_R$=11.87 min.

EXAMPLE 12

$N^\alpha$[N-(1H-indol-3-yl-carbonyl)-(R,S)cis-2-amino (3,4 dehydro)cyclohexyl-carbonyl]-L-3(2-naphthyl) alanyl-N-methyl-N-benzylamide and $N^\alpha$[N-(1H-indol-3-yl-carbonyl)-(S,R)cis-2-amino(3,4 dehydro) cyclohexyl-carbonyl]-L-3-(2-naphthyl)alanyl-N-methyl-N-benzylamide HPLC: (System 1) fast: $T_R$=26.42 min slow $T_R$=27.38 min; TLC($SiO_2$) $CHCl_3/CH_3OH$ (9:1 v/v) $R_f$=0.43 and 0.43.

EXAMPLE 13

$N^\alpha$[N-(1H-indol-3-yl-carbonyl)-(R,S)cis-2-aminocyclohexylcarbonyl]-L-2 phenylglicyl-N-methyl-N-benzylamide and $N^\alpha$[N-(1H-indol-3-yl-carbonyl)-(S,R)cis-2-aminocyclohexyl-carbonyl]-L-2 phenylglicyl-N-methyl-N-benzylamide HPLC: (System 2) isocratic 60% B: fast: $T_R$=9.26 min slow $T_R$=10.90 min.

EXAMPLE 14

N$^\alpha$[N-(1H-indol-3-yl-carbonyl)-(R,S)cis-2-aminocyclohexylcarbonyl]-L-3-Cyclohexyl alanyl-N-methyl-N-benzylamide and N$^\alpha$[N-(1H-indol-3-yl-carbonyl)-(S,R)cis-2-aminocyclohexyl carbonyl]-L-3 Cyclohexyl alanyl-N-methyl-N-benzylamide HPLC: (System 2) isocratic 45% B: fast: T$_R$=8.26 min slow T$_R$=15.26 min.

EXAMPLE 15

N$^\alpha$[N-(1H-indol-3-yl-carbonyl)-(R,S)cis-2-aminocyclohexylcarbonyl]-L-3-(1-naphthyl)alanyl-N-methyl-N-benzylamide and N$^\alpha$[N-(1H-indol-3-yl-carbonyl)-(S,R)cis-2-aminocyclohexylcarbonyl]-L-3-(1-naphthyl)alanyl-N-methyl-N-benzylamide HPLC: (system 2) isocratic 60% B: fast: T$_R$=10.22 min slow T$_R$=11.96 min.

EXAMPLE 16

N$^\alpha$[N-(1H-indol-3-yl-carbonyl)-(R,S)cis-2-aminocyclohexylcarbonyl]-D-3-(2-naphthyl)alanyl-N-methyl-N-benzylamide and N$^\alpha$[N-(1H-indol-3-yl-carbonyl)-(S,R)cis-2-aminocyclohexylcarbonyl]-D-3-(2-naphthyl)alanyl-N-methyl-N-benzylamide HPLC: (System 2) isocratic 45% B: fast: T$_R$=8.26 min slow T$_R$=15.26 min.

EXAMPLE 17

N$^\alpha$[N-(benzoyl)-(R,S)cis-2-aminocyclohexyl-carbonyl]-D-3-(2-naphthyl)alanyl-N-methyl-N-benzylamide and N$^\alpha$[N-(benzoyl)-(S,R)cis-2-aminocyclohexyl-carbonyl]-D-3-(2-naphthyl)alanyl-N-methyl-N-benzylamide HPLC: (System 2) isocratic 70% B: fast: T$_R$=11.06 min slow T$_R$=18.82 min.

Assessment of biological activity (NK1 antagonism) of compounds of this invention was performed by means of the following binding and functional assays:
[3H] SP binding assay in IM9 Cell Line Binding assay was performed with intact cells as described by Payan et al. (J. Immunology 133, 3260 (1984)). Cells were washed with buffer A, (pH 7.5), containing (in mM) Tris-HCl 50, and NaCl 150, plus 0.02% BSA, and then resuspended in assay buffer (buffer A supplemented with protease inhibitors) at a concentration of 1×10$^7$ cells/ml. Cells were incubated with [3H]SP in a final volume of 0.5 ml for 60 min. at room temperature. Nonspecific binding was determined in the presence of 10 mM nonradioactive SP. The assay mixture was set up in microfuge tubes that had been presoaked in a 0.5% BSA solution for at least 3 hours. Bound and free [$^3$H]SP were separated by pelleting the cells in a microfuge (6 min.; 12000 g); the supernatant was then removed by aspiration. For competition binding experiments, IM9 cells were incubated in triplicate with nM [$^3$H]SP (the approximate Kd value, as determined in saturation binding experiments); competing ligands were typically added in six concentrations (1:10 dilutions in assay buffer) to give full competition curves.

Measurement of pA$_2$ in isolated guinea pig ileum

Male albino guinea-pigs weighing 300–350 g were stunned and bled. A segment of ileum was excised and placed in oxygenated Krebs solution containing 10 mM indomethacin. The longitudinal muscle with attached myenteric plexus was then removed, the longitudinal muscle-myenteric plexus was discarded and a ring approximately 3 mm wide was excised and used for subsequent experiments. Ileal rings were suspended in 5-ml organ baths by means of two stainless steel hooks and connected to an isotonic transducer (load 5 mN). After 90 min. equilibration period a cumulative concentration-response curve for the agonist, [Sar$^9$]substance P sulfone was made. After two or more reproducible control curves for the agonist had been obtained, the compound to be tested was added to the bath and a new curve for the agonist was determined in its presence.

Regression analysis was performed by the least-squares method. EC$_{50}$ values and 95% confidence limits (c.I.) were calculated. Schild plots were constructed and if the slope was not significantly different from unity, pA$_2$ values were calculated by using the constrained Schild plot method.

The data in Table I were obtained for compound of formula (I):

TABLE I

| Substance P antagonism Results | |
|---|---|
| Compound of Ex # | % of binding inhibition at 1 μM |
| 1 fast | 96% |
| 2 fast | 100% |
| 3 fast | 100% |
| 10 fast | 95% |
| 17 fast | 98% |

We claim:

1. A tachyquinine antagonist compound having general formula (I)

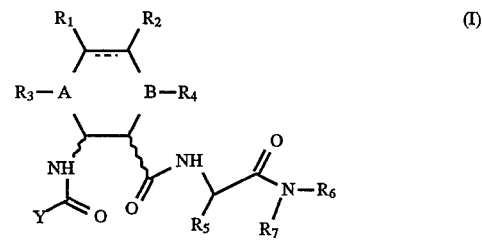

wherein:

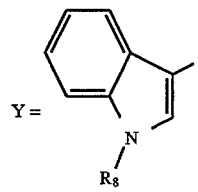

where

R$_8$ is selected from the group consisting of H, a linear or branched alkyl radical containing 1 to 6 carbon atoms, a linear or branched alkenyl radical containing 2 to 7 carbon atoms, a linear or branched alkynyl radical containing 3 to 7 carbon atoms, a cycloalkyl radical containing 3 to 6 carbon atoms, wherein optionally at least one of the 3 to 6 carbon atoms is replaced with an atom selected from the a group consisting of N, S, and O and an aryl-, aryl-alkyl-, or alkyl-aryl-radical containing 7 to 12 carbon atoms; the symbol ═ represents a single or a double bond; if the bond is single, $R_1$ and $R_2$ are selected from the group consisting of hydrogen, hydroxyl and halogen or are joined to form an epoxide; if the bond is double, $R_1$ and $R_2$ are hydrogen or halogen; A and B stand for N or CH; $R_3$ and $R_4$ are selected from the group consisting of hydrogen, a linear or branched alkyl radical containing 1 to 6 carbon atoms, a linear or branched alkenyl radical containing 2 to 7 carbon atoms, a linear or branched alkynyl radical containing 3 to 7 carbon atoms, or are joined together to form a —$(CH_2)_n$— bridge, where n stands for a whole number from 1 to 3;

$R_5$ stands for an alkyl-, aryl-, aryl-alkyl-, or alkyl-aryl-radical with up to 15 carbon atoms;

$R_6$ and $R_7$ are selected from the group consisting of hydrogen, an alkyl-, aryl-, aryl-alkyl-, alkyl-aryl-radical, and the symbol ∽∽∽ means that the configuration of the asymmetric carbon atoms of 2-amino-cyclohexanecarboxylic acid is S or R provided that such configuration cannot be S or R for both the asymmetric carbon atoms.

2. The compound according to claim 1, wherein $R_8$=H; $R_5$ and $R_6$=

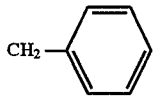

and the configuration of the asymmetric carbon atoms of 2-amino cyclohexanecarboxylic acid is S or R.

3. A compound according to claim 1, wherein the alkyl radical is selected from the group consisting of methyl, ethyl, propyl, butyl, and pentyl; the alkenyl radical is selected from the group consisting of propenyl and butenyl; the alkynyl radical is propynyl; the alkyl moiety of the alkyl-aryl-, and aryl-alkyl radicals is an alkyl radical as defined above; the aryl moiety of the aryl-, alkyl-aryl- and aryl-alkyl-radicals is selected from the group consisting of pyridine, benzofuran, benzene, indole, naphthyl, tetrahydroquinoline, imidazole, tetrahydroindoline; the cycloalkyl radical, is selected from the group consisting of cyclohexane, cyclopentane, cycloheptane, cyclooctane, piperidine, morpholine, piperazine, and pyrazine.

4. A compound according to claim 1 represented by:

N-methyl-N-benzylamide of $N^\alpha$-{[N(indol-3-yl-carbonyl) (R,S)cis-2-amino]cyclohexanoyl}-L-phenylalanine and N-methyl-N-benzylamide of $N^\alpha$-{[N(indolin-3-yl-carbonyl)(S,R)cis-2-amino]cyclohexanoyl}-L-phenylalanine;

$N^\alpha$[N-(1H-indol-3-yl-carbonyl)-(R,S)cis-2-aminocyclohexyl-carbonyl]-L-3(2-naphthyl)alanyl-N-methyl-N-benzylamide and $N^\alpha$[N-(1H-indol-3-yl-carbonyl)-(S,R)cis-2-aminocyclohexyl-carbonyl]-L-3(2-naphthyl)alanyl-N-methyl-N-benzylamide;

$N^\alpha$[N-(1H-indol-3-yl-carbonyl)-(R,S)cis-2-aminocyclohexyl-carbonyl]-L-2-phenylalanyl-N-benzylamide and $N^\alpha$[N-(1H-indol-3-yl-carbonyl)-(S,R) cis-2-aminocyclohexyl-carbonyl]-L-2-phenylalanyl-N-benzylamide;

$N^\alpha$[N-(1H-indol-3-yl-carbonyl)-(R,S)cis-2-aminocyclohexyl-carbonyl]-L-phenylalanyl-N,N dibenzylamide and $N^\alpha$[N-(1H-indol-3-yl-carbonyl)-(S,R)cis-2-aminocyclohexan-carboxyl]-L-phenylalanyl-N,N dibenzylamide;

$N^\alpha$[N-(1-(methyl)indol-3-yl-carbonyl)-(R,S)cis-2-aminocyclohexylcarbonyl]-L-3(2-naphthyl)alanyl-N-methyl-N-benzylamide and $N^\alpha$[N-(1-(methyl)indol-3-yl-carbonyl)-(S,R)cis-2-aminocyclohexylcarbonyl]-L-3(2-naphthyl)alanyl-N-methyl-N-benzylamide;

$N^\alpha$[N-(1-(methyl)-indol-3-yl-carbonyl)-(R,S)cis-2-aminocyclohexylcarbonyl]-L-phenylalanyl-N-methyl-N-benzylamide;

$N^\alpha$[N-(1H-indol-3-yl-carbonyl)-(R,S)cis-2-aminocyclohexyl-carbonyl]-L-phenylalanyl-N,N dimethylamide and $N^\alpha$[N-(1H-indol-3-yl-carbonyl)-(S,R)cis-2-aminocyclohexan-carboxyl]-L-phenylalanyl-N,N dimethylamide;

$N^\alpha$[N-(1H-indol-3-yl-carbonyl)-(R,S)cis-2-aminocyclohexyl-carbonyl]-L-phenylalanyl-tetrahydroisoquinolide and $N^\alpha$[N-(1H-indol-3-yl-carbonyl)-(S,R)cis-2-aminocyclohexan-carboxyl]-L-phenylalanyltetrahydroisoquinolide;

$N^\alpha$[N-(1H-indol-3-yl-carbonyl)-3S-endo-aminobicyclo(2,2,1)heptyl-2R-endo-carbonyl]-L-3-(2-naphthyl)alanyl-N-methyl-N-benzylamide and $N^\alpha$[N-(1H-indol-3-yl-carbonyl)-3R-endo-aminobicyclo(2,2,1)heptyl-2S-endo-carbonyl]-L-3-(2-naphthyl)alanyl-N-methyl-N-benzylamide;

$N^\alpha$[N-(1H-indol-3-yl-carbonyl)-3S-exo-aminobicyclo(2,2,1)heptyl-2R-exo-carbonyl]-L-3-(2-naphthyl)alanyl-N-methyl-N-benzylamide and $N^\alpha$[N-(1H-indol-3-yl-carbonyl)-3R-endo aminobicyclo (2,2,1)heptyl-2S-exo carbonyl]-L-3-(2-naphthyl)alanyl-N-methyl-N-benzylamide;

$N^\alpha$[N-(1H-indol-3-yl-carbonyl)-(R,S)cis-2-amino(3,4 dehydro)cyclohexyl-carbonyl]-L-3(2-naphthyl)alanyl-N-methyl-N-benzylamide and $N^\alpha$[N-(1H-indol-3-yl-carbonyl)-(S,R)cis-2-amino (3,4 dehydro)cyclohexyl-carbonyl]-L-3-(2-naphthyl)alanyl-N-methyl-N-benzylamide;

$N^\alpha$[N-(1H-indol-3-yl-carbonyl)-(R,S)cis-2-aminocyclohexyl-carbonyl]-L-2 phenylglicyl-N-methyl-N-benzylamide and $N^\alpha$[N-(1H-indol-3-yl-carbonyl)-(S,R)cis-2-aminocyclohexyl-carbonyl]-L-2 phenylglicyl-N-methyl-N-benzylamide;

$N^\alpha$[N-(1H-indol-3-yl-carbonyl)-(R,S)cis-2-aminocyclohexyl-carbonyl]-L-3-Cyclohexyl-alanyl-N-methyl-N-benzylamide and $N^\alpha$[N-(1H-indol-3-yl-carbonyl)-(S,R)cis-2-aminocyclohexyl carbonyl]-L-3-Cyclohexyl-alanyl-N-methyl-N-benzylamide;

$N^\alpha$[N-(1H-indol-3-yl-carbonyl)-(R,S)cis-2-aminocyclohexylcarbonyl]-L-3-(1-naphthyl)alanyl-N-methyl-N-benzylamide and $N^\alpha$[N-(1H-indol-3-yl-carbonyl)-(S,R)cis-2-aminocyclohexylcarbonyl]-L-3-(1-naphthyl)alanyl-N-methyl-N-benzylamide;

$N^\alpha$[N-(1H-indol-3-yl-carbonyl)-(R,S)cis-2-aminocyclohexylcarbonyl]-D-3-(2-naphthyl)alanyl-N-methyl-N-benzylamide and $N^\alpha$[N-(1H-indol-3-yl-carbonyl)-(S,R)cis-2-aminocyclohexylcarbonyl]-D-3-(2-naphthyl)alanyl-N-methyl-N-benzylamide;

$N^\alpha$[N-(benzoyl)-(R,S)cis-2-aminocyclohexyl-carbonyl]-D-3-(2-naphthyl)alanyl-N-methyl-N-benzylamide and $N^\alpha$[N-(benzoyl)-(S,R)cis-2-aminocyclohexyl-carbonyl]-D-3-(2-naphthyl)alanyl-N-methyl-N-benzylamide.

5. Pharmaceutical composition containing, as active ingredient, an effective dose of compound according to claim 1.

6. Pharmaceutical composition containing, as active ingredient, an effective dose of compound according to claim 2.

7. A process for the preparation of tachyquinine antagonist compound having general formula (I)

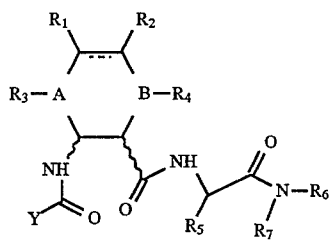

wherein:

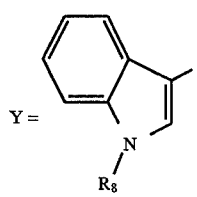

where

R$_8$ is selected from the group consisting of H, a linear or branched alkyl radical containing 1 to 6 carbon atoms, a linear or branched alkenyl radical containing 2 to 7 carbon atoms, a linear or branched alkynyl radical containing 3 to 7 carbon atoms, a cycloalkyl radical containing 3 to 6 carbon atoms, and an aryl-, aryl-alkyl-, or alkyl-aryl radical containing 7 to 12 carbon atoms; the symbol ⎓ represents a single or a double bond; if the bond is single, R$_1$ and R$_2$ are selected from the group consisting of hydrogen, hydroxyl and halogen or are joined to form an epoxide; if the bond is double, R$_1$ and R$_2$ are hydrogen or halogen; A and B stand for N or CH; R$_3$ and R$_4$ are selected from the group consisting of hydrogen, a linear or branched alkyl radical containing 1 to 6 carbon atoms, a linear or branched alkenyl radical containing 2 to 7 carbon atoms, a linear or branched alkynyl radical containing 3 to 7 carbon atoms, or are joined together to form a —(CH$_2$)$_n$— bridge, where n stands for a whole number from 1 to 3;

R$_5$ stands for an alkyl, aryl, aryl-alkyl, or alkyl-aryl radical with up to 15 carbon atoms;

R$_6$ and R$_7$ are selected from the group consisting of hydrogen, an alkyl, aryl, aryl-alkyl, and alkyl-aryl radical, and the symbol ∿∿∿ means that the configuration of the asymmetric carbon atoms of 2-amino-cyclohexanecarboxylic acid is S or R, provided that such configuration cannot be S or R for both the asymmetric carbon atoms, comprising the steps of:

a) condensing, in the presence of a suitable condensing agent, intermediate of formula (II)

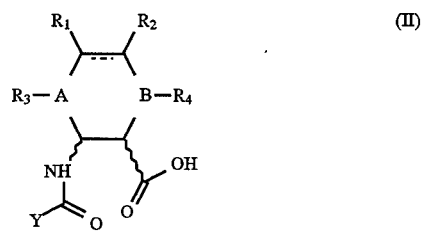

with intermediate of formula (III)

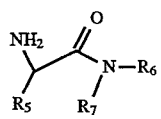

where R$_1$, R$_2$, R$_3$, R$_4$, R$_5$, R$_6$, R$_7$, Y, A, and B are as defined above, wherein said compound of formula (II) is prepared by condensation, in the presence of a suitable condensing agent, of a compound of general formula (IV) with a compound of general formula (V),

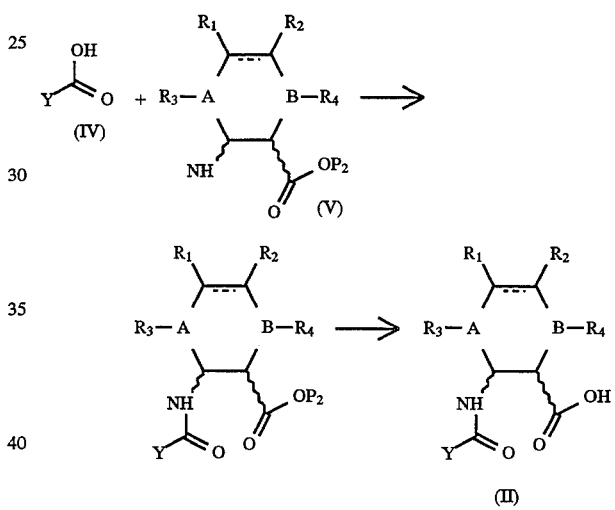

where R$_1$, R$_2$, R$_3$, R$_4$, Y, A, and B are as defined above and P$_2$ is a group that temporarily protects the carboxylic group, followed by elimination of the P$_2$ protecting group and said compound of general formula (III) is prepared by condensation of a compound of general formula (VI) and a compound of general formula (VII)

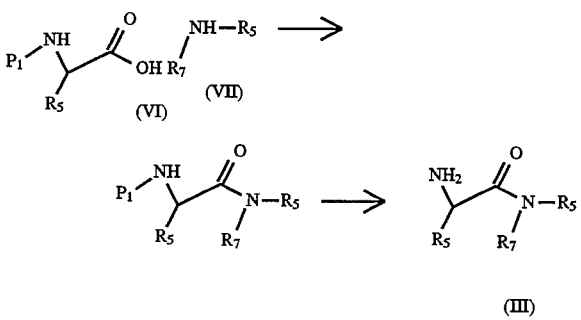

where R$_5$, R$_6$, R$_7$, R$_8$ are as defined above and P$_1$ is a protecting group for the α-amino group, selected from the groups commonly used in classical peptide syntheses, which can be easily removed under conditions not causing the partial or total opening of the bond between $R_6$, $R_7$ and nitrogen, said condensation being carried out in the presence of aprotic polar organic solvents;

b) eliminating the reaction by-products by evaporation of the reaction solvent and treatment of the residue, or a solution of same in a suitable organic solvent, with slightly acid or slightly basic aqueous solutions;

c) separating the residue obtained under b) by chromatography or crystallization.

8. A compounds of general formula (II)

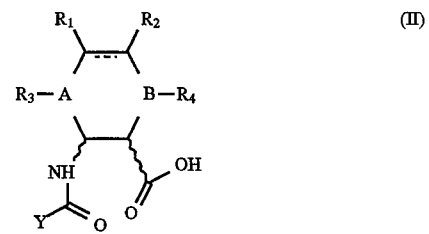

where $R_1$, $R_2$, $R_3$, $R_4$, A, B and Y are as defined in claim 1.

* * * * *